United States Patent [19]

Dell et al.

[11] Patent Number: 5,284,868
[45] Date of Patent: Feb. 8, 1994

[54] PHARMACEUTICAL COMPOUNDS

[75] Inventors: Colin P. Dell, Dorking, England; Jai P. Singh, Carmel, Ind.; Colin W. Smith, Bracknell, England

[73] Assignees: Eli Lilly and Company, Indianapolis, Ind.; Lilly Industries Limited, Basingstoke, England

[21] Appl. No.: 951,629

[22] Filed: Sep. 25, 1992

[30] Foreign Application Priority Data

Oct. 9, 1991 [GB] United Kingdom ............... 9121358.7
Jun. 19, 1992 [GB] United Kingdom ............... 9213058.2

[51] Int. Cl.$^5$ .................... C07D 311/92; A61K 31/35
[52] U.S. Cl. .................................. 514/454; 514/314; 514/320; 514/337; 514/394; 514/443; 514/444; 514/455; 546/167; 546/196; 546/269; 548/525; 548/305.1; 549/51; 549/58; 549/60; 549/389
[58] Field of Search ............... 549/389, 51, 58, 60; 546/167, 196, 269; 548/325, 327, 525; 514/314, 320, 337, 394, 443, 444, 454, 455

[56] References Cited

PUBLICATIONS

Elnagdi et. al., *Naturforschung B*, 47(4), pp. 572–578 (Apr. 1992).
Elagamey et. al., *Indian J. of Chem.*, 29B, pp. 885–886 (1990).
Elagamey et. al., *Collection of Czechoslovak Chem. Commun.*, 53, pp. 1534–1538 (1988).
Reaktionen, *Monatshefte fur Chemie*, 110, 115–119 and 249–256 (1979).
Otto, et al., *Arch. Pharm.*, 312(6), 548–550 (1979).

*Primary Examiner*—Bernard Dentz
*Attorney, Agent, or Firm*—Steven P. Caltrider; Leroy Whitaker

[57] ABSTRACT

A pharmaceutical compound of the formula

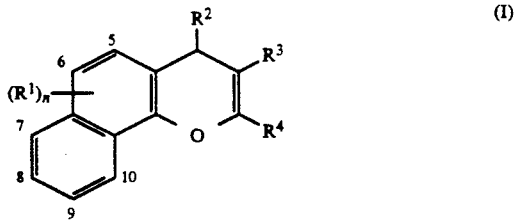

in which n is 0, 1 or 2 and $R^1$ is attached at any of the positions 5, 6, 7, 8, 9 or 10, and each $R^1$ is halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^5$ where $R^5$ is an ester group, —$CONR^6R^7$ or —$NR^6R^7$ where $R^6$ and $R^7$ are each hydrogen or $C_{1-4}$ alkyl; $R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl; $R^3$ is nitrile, carboxy, —$COOR^8$ where $R^8$ is an ester group, —$CONR^9R^{10}$ where $R^9$ and $R^{10}$ are each hydrogen or $C_{1-4}$ alkyl, or $R^{11}SO_2$— where $R^{11}$ is $C_{1-4}$ alkyl or optionally substituted phenyl; and $R^4$ is —$NR^{12}R^{13}$, —$NHCOR^{12}$, —$N(COR^{12})_2$ or —$N=CHOCH_2R^{12}$ where $R^{12}$ and $R^{13}$ are each hydrogen or $C_{1-4}$ alkyl optionally substituted with carboxy,

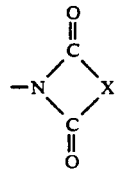

where X is $C_{2-4}$ alkylene, or —$NHSO_2R^{14}$ where $R^{14}$ is $C_{1-4}$ alkyl or optionally substituted phenyl; provided that when n is 0, $R^3$ is nitrile and $R^4$ is —$NH_2$, $R^2$ is not phenyl or phenyl substituted in the para-position with a single chloro, hydroxy or methoxy substituent; and salts thereof.

15 Claims, No Drawings

PHARMACEUTICAL COMPOUNDS

This invention relates to pharmaceutical compounds, their preparation and use.

The synthesis of certain phenyl-substituted naphtho [1,2-b] pyrans is described by Elagamey A. et al in Indian Journal of Chemistry, 29B, 885–886, (1990), and Collection Czechoslovak Chem. Commun., 53(7), 1534–1538, (1988). No biological properties or activity are ascribed to the compounds disclosed.

The compounds of the invention have the formula:

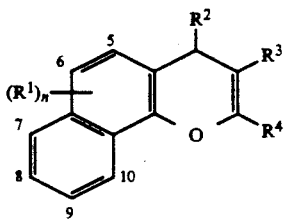

in which n is 0, 1 or 2 and $R^1$ is attached at any of the positions 5, 6, 7, 8, 9 or 10, and each $R^1$ is halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^5$ where $R^5$ is an ester group, —$CONR^6R^7$ or —$NR^6R^7$ where $R^6$ and $R^7$ are each hydrogen or $C_{1-4}$ alkyl; $R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl; $R^3$ is nitrile, carboxy, —$COOR^8$ where $R^8$ is an ester group, —$CONR^9R^{10}$ where $R^9$ and $R^{10}$ are each hydrogen or $C_{1-4}$ alkyl, or $R^{11}SO_2$— where $R^{11}$ is $C_{1-4}$ alkyl or optionally substituted phenyl; and $R^4$ is —$NR^{12}R^{13}$, —$NHCOR^{12}$, —$N(COR^{12})_2$ or —$N=CHOCH_2R^{12}$ where $R^{12}$ and $R^{13}$ are each hydrogen or $C_{1-4}$ alkyl optionally substituted with carboxy,

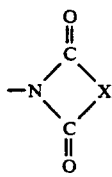

where X is $C_{2-4}$ alkylene, or —$NHSO_2R^{14}$ where $R^{14}$ is $C_{1-4}$ alkyl or optionally substituted phenyl; provided that when n is 0, $R^3$ is nitrile and $R^4$ is —$NH_2$, $R^2$ is not phenyl or phenyl substituted in the para-position with a single chloro, hydroxy or methoxy substituent; and salts thereof.

The compounds of the invention have been found to be active in tests which show their potential for treatment of immune diseases and diseases in which excess cell proliferation or enzyme release play a significant role.

In the above formula (I), halo is, for example, fluoro, chloro or bromo and is especially chloro. A $C_{1-4}$ alkyl group includes, for example, methyl, ethyl, propyl and butyl, and is preferably methyl or ethyl. A $C_{1-4}$ alkoxy group is one such alkyl group linked through oxygen to an aryl nucleus. A hydroxyalkyl group is one such alkyl group substituted with a hydroxyl, and preferably of the formula $HO(CH_2)_x$—where x is 1 to 4. A hydroxyalkoxy group is an alkoxy group substituted with a hydroxyl, and preferably of the formula $HO(CH_2)_xO$—where x is 1 to 4. $C_{1-4}$ alkylthio is $C_{1-4}$ alkyl linked via a sulphur atom.

A substituted phenyl group is substituted with one or more, preferably one or two substituents each selected from halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^{15}$ where $R^{15}$ is an ester group, —$CONR^{16}R^{17}$ or —$NR^{16}R^{17}$ where $R^{16}$ and $R^{17}$ are each hydrogen or $C_{1-4}$ alkyl. Substituted naphthyl and heteroaryl groups may be similarly substituted. In addition substituted phenyl includes a phenyl group in which neighbouring atoms are substituted by —$O(CH_2)_mO$—, where m is 1, 2 or 3.

When n is 1 or 2 and there are one or two substituents on the naphtho nucleus they can be at any of the positions 5 to 10. When there are two substituents they can be the same or different. It is preferred that the naphtho nucleus is unsubstituted or that it bears a single substituent at the 5, 6 or 9-positions.

When $R^2$ is heteroaryl it is preferably 2-thienyl, 3-thienyl, 2-pyridyl, 3-pyridyl, 4-pyridyl, 2-benzothienyl, 3-benzothienyl, 2-quinolinyl, 3-quinolinyl, 2-benzofuranyl, 3-benzofuranyl or 2-benzidimazolyl, 2-furanyl or 3-furanyl. A naphthyl group is attached at the 1- or 2-position. Such groups can be substituted at any of the available positions, but are preferably unsubstituted.

A preferred value of $R^2$ is optionally substituted phenyl, preferably phenyl with a single substituent, especially nitro or trifluoromethyl.

The group $R^3$ is preferably nitrile. When $R^3$ is —$COOR^8$, $R^8$ can be any ester group and is preferably $C_{1-4}$ alkyl, especially methyl or ethyl.

The group $R^4$ is preferably —$NR^{12}R^{13}$, and especially —$NH_2$.

A particular group of compounds according to formula (I) are compounds to which n is 0, 1 or 2 and $R^1$ is attached at any of the positions 5, 6, 7, 8, 9 or 10, and each $R^1$ is halo, trifluoromethyl or $C_{1-4}$ alkoxy, $R^2$ is phenyl, naphthyl or heteroaryl optionally substituted with one or two substituents each selected from nitro, trifluoromethyl, halo, $C_{1-4}$ alkyl and $C_{1-4}$ alkoxy or $R^2$ is furanyl optionally substituted with $C_{1-4}$ alkyl, $R^3$ is nitrile, carboxy, —$COOR^8$ where $R^8$ is an ester group, or —$CONR^9R^{10}$ where $R^9$ and $R^{10}$ are each hydrogen or $C_{1-4}$ alkyl, and $R^4$ is —$NR^{12}R^{13}$, —$NHCOR^{12}$ or —$N(COR^{12})_2$ where $R^{12}$ and $R^{13}$ are each hydrogen or $C_{1-4}$ alkyl, or —$NHSO_2R^{14}$ where $R^{14}$ is $C_{1-4}$ alkyl or phenyl optionally substituted with one to three substituents each selected from $C_{1-4}$ alkyl, $C_{1-4}$ alkoxy, nitro and halo; provided that when n is 0, $R^3$ is nitrile and $R^4$ is —$NH_2$, $R^2$ is not phenyl or phenyl substituted in the para-position with a single chloro, hydroxy or methoxy substituent.

An especially preferred group of compounds is of the formula

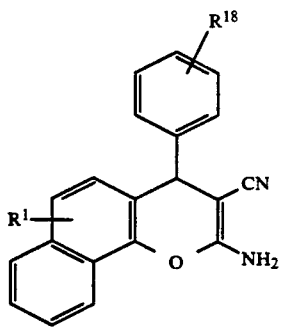

where $R^1$ is hydrogen, $C_{1-4}$ alkoxy or halo, and $R^{18}$ is nitro or trifluoromethyl. The $R^1$ group is preferably attached at the 5, 6 or 9 positions.

It will be appreciated that when, for example, $R^1$ or $R^3$ is —COOH, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

When $R^1$ and $R^3$ are —COOR$^5$ and —COOR$^8$ respectively, the compounds are in ester form. The ester group can be any conventional group, for example, an ester derived from an alcohol, especially a $C_{1-4}$ alcohol. Preferred values of $R^5$ and $R^8$ are thus $C_{1-4}$ alkyl.

It will be appreciated that the compounds of the invention contain an asymmetric carbon atom which gives rise to enantiomers. The compounds are normally prepared as racemates and can conveniently be used as such but individual enantiomers can be isolated by conventional techniques if so desired. Such racemates and individual enantiomers form part of the present invention.

The invention also comprises a process for producing a compound of formula (I) above, which comprises (1) reacting a compound of the formula

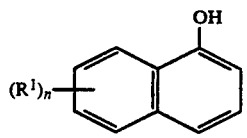

with a compound of the formula

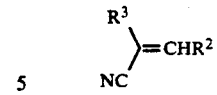

to give a compound of formula (I) in which $R^4$ is —NH$_2$, or (2) converting a compound of the formula

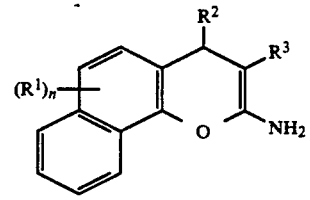

to a compound of formula (I) in which $R^4$ IS —NR$^{12}$R$^{13}$, —NHCOR$^{12}$, —N(COR$^{12}$)$_2$, —N=CHOCH$_2$R$^{12}$, —NHSO$_2$R$^{14}$ or

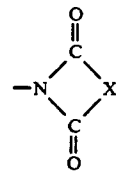

With regard to process (1), the reaction is preferably carried out at a temperature of from 0° C. to 100° C. and in the presence of an organic solvent, such as for example ethanol. Compounds of formula (II) are known or can be easily synthesised by known methods.

The reactants of formula (III) can be prepared by reacting the appropriate nitrile of the formula

R$^3$CH$_2$CN with an aldehyde of the formula

R$^2$CHO preferably at a temperature of from 20° C. to 100° C. in the presence of an organic base as catalyst such as piperidine and in the presence of an organic solvent, such as for example ethanol. The nitrile and aldehyde reactants are known compounds or can be made by methods known in the art.

With regard to process (2), the free enamine can be prepared by reaction (1) and subsequently converted to compounds in which $R^4$ takes other values. For example, the free amino group can be alkylated with reagents of formula R$^{12}$X or R$^{13}$X where X is halogen, or (R$^{12}$)$_2$SO$_4$ or (R$^{13}$)$_2$SO$_4$ to give the mono- or dialkylated product. Similarly the amino group can be acylated with an acyl halide or an acid anhydride such as R$^{12}$COX or (R$^{12}$CO)$_2$O to give compounds in which $R^4$ is —NHCOR$^{12}$ or —N(COR$^{12}$)$_2$. Compounds in which $R^4$ is —N=CHOCH$_2$R$^{12}$ are prepared by reaction with the appropriate trialkyl orthoformate, and those in which $R^4$ is —NHSO$_2$R$^{14}$ by reaction with a sulphonyl halide of formula R$^{14}$SO$_2$X.

As mentioned above, the compounds have pharmaceutical activity. They have an antiproliferative effect on cell division, and are thus indicated for use in the treatment of diseases where excess cell proliferation or enzyme release is an important aspect of the pathology.

For example, the compounds of the invention inhibit the natural proliferation of 3T3 fibroblasts at $IC_{50}$ concentrations of below $10\mu$ molar.

Furthermore, the compounds have been shown to modify the immune response by inhibiting concanavalin A-induced T-cell proliferation in the test described by Lacombe P. et al, FEBS, 3048, 191, 227-230. In general the compounds of the invention have an $IC_{50}$ value in this test of below 10 $\mu$M.

The compounds also inhibit cell proliferation in an NS-1 murine B-lymphoma line, and phorbol ester-stimulated plasminogen activator synthesis in bovine retinal capillary endothelial cells.

Inhibition of macrophage-conditioned medium induced neutral protease release in chondrocytes has also been observed in the test described by K. Deshmukh-Phadke, M. Lawrence and S. Nanda, *Biochem. Biophys. Res. Commun.*, 1978, 85, 490-496.

Such properties show that the compounds have potential in the treatment of a wide range of diseases, such as for example rheumatoid arthritis, atherosclerosis, cirrhosis, fibrosis and cancer, and for the treatment of auto-immune diseases, such as for example systemic lupus, and in the prevention of graft rejection. They are also indicated for the treatment of osteoarthritis and diabetic complications.

Furthermore, compounds of the invention have been shown to inhibit vascular smooth cell proliferation. This has been demonstrated by using cultured smooth cells derived from rabbit aortae, proliferation being determined by the measurement of DNA synthesis. Cells are obtained by explant method as described in Ross, *J. of Cell Bio.* 50:172 (1971). Cells are plated in 96 well microtiter plates for five days. The cultures become confluent and growth is arrested. The cells are then transferred to Dulbecco's Modified Eagle's Medium (DMEM) containing 0.5-2% platelet poor plasma, 2 mM L-glutamine, 100 U/ml penicillin, 100 $\mu$g ml streptomycin, 1 $\mu$C/ml $^3$H-thymidine, 20 ng/ml platelet-derived growth factor and varying concentrations of the compounds. Stock solution of compounds is prepared in dimethyl suphoxide and then diluted to appropriate concentration (0.01-10 $\mu$g/ml) in the above assay medium. Cells are then incubated at 37° C. for 24 hours under 5% $CO_2$/95% air. At the end of 24 hours, the cells are fixed in methanol. $^3$H thymidine incorporation in DNA was then determined by scintillation counting as described in Bonin et al., *Exp. Cell Res.* 181: 475-482 (1989).

Inhibition of smooth muscle cell proliferation by the compounds of the invention is further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 $\mu$g/ml streptomycin. After 24 hours, the cells are attached, the medium is replaced with DMEM containing 2% platelet poor plasma, 2 mM L-glutamine, 100 U/ml penicillin, 100 $\mu$g/ml steptomycin, 40 ng/ml platelet-derived growth factor and indicated concentrations of the compounds. Cells are allowed to grow for four days. Cells are treated with trypsin. The number of cells in each cultures is determined by counting using a ZM-Coulter counter.

Activity in the above tests indicates that the compounds of the invention are of potential in the treatment of restenosis, which is characterised by the migration and proliferation of smooth muscle cells in response to injury. Thus the invention specifically provides a method of treating restenosis, which comprises administering to a patient in need of treatment a therapeutic dosage of a compound of the formula (I).

The invention also includes a pharmaceutical composition comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc magnesium stearate and mineral oil. The compositions of the injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

In the treatment of restenosis the administration of a compound of the invention may be local or systemic delivery. Systemic delivery includes techniques that introduce the compound to the entire organism. Examples of systemic delivery include oral and intravenous administration, previously discussed.

The local delivery of a compound of the invention may be by a variety of techniques which administer the compound at or near the proliferative site.

Examples of local delivery techniques are not intended to be limiting but to be illustrative of the techniques available. Examples include local delivery catheters, site specific carriers, implants, or direct injection.

Local delivery by a catheter allows the administration of a pharmaceutical agent directly to the proliferative lesion. Examples of local delivery using a balloon catheter are described in EP 0 383 492 A2 and U.S. Pat. No. 4,636,195 (Wolinsky, Jan. 13, 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Langer, *Science* 249: 1527–1533 (September 1990). An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October 1990). A second example is a delivery system in which a polymer that contains the pharmaceutical agent is injected into the lesion in liquid form. The polymer then cures to form the implant in situ. This technique is described in PCT WO 90/03768 (Donn, Apr. 19, 1990). Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989). A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September 1990) and Mathiowitz, et al., *J. App. Poly. Sci.*, 26: 809 (1981).

Local delivery by site specific carriers describes attaching the pharmaceutical agent to a carrier which will direct or link the drug to the proliferative cells. Examples of this delivery technique includes the use of carriers such as a protein ligand, a monoclonal antibody or a membrane anchored linker. Lange, *Science* 249: 1527–1533 (September 1990); Langworth, *Genetic Engineering News* (September 1990).

Local delivery by direct injection describes injecting fine particles of the compound suspended in an inert carrier such as sterile saline solution directly into the proliferative region.

The examples of local delivery are merely illustrative and are not mutually exclusive. For example, the delivery of microparticles to the proliferative smooth muscle cells may be by a local delivery catheter or direct injection.

The dosage of a compound of the invention for treatment of restenosis is dependent upon the method of administration and the particular circumstances of the patient. A therapeutic dosage is a amount sufficient to inhibit the migration and proliferation of vascular smooth muscle cells. The preferred dosage range is defined to be about 1 μg/day to about 500,000 μg/day delivered at or near the proliferative site.

The term 'treating' includes the administration of a compound of present invention to prevent the onset of the symptoms, alleviating the symptoms, or eliminating the disease, condition or disorder.

The invention is illustrated by the following Examples.

EXAMPLE 1

3-(Trifluoromethyl)-benzaldehyde (9.2 g) and ethyl cyanoacetate (5.3 ml) were dissolved in ethanol (20 ml) and this solution was heated to reflux temperature. Heating was discontinued, piperidine (two drops) was added, and once the vigour of the reaction began to subside heating was recommenced and maintained at reflux temperature for one hour. The solution was chilled, using an ice-water bath, water (30 ml) was added and white crystals of ethyl 2-cyano-3-[3-(trifluoromethyl)-phenyl)]-propenoate were filtered off, washed with water and dried, m.p. 79° C.

The following compounds were prepared in a similar manner:

Ethyl 2-cyano-3-[4-(trifluoromethyl)phenyl]-propenoate, m.p. 114° C.
Ethyl 2-cyano-3-[2-(trifluoromethyl)phenyl]-propenoate, m.p. 74° C.
2-Nitrobenzylidenamalononitrile, m.p. 141° C.
3-Nitrobenzylidenemalononitrile, m.p. 108° C.
4-Nitrobenzylidenemalononitrile, m.p. 162° C.
3-Chlorobenzylidenemalononitrile, m.p. 118° C.
3-Fluorobenzylidenemalononitrile, m.p. 91° C.
3-Bromobenzylidenemalononitrile, m.p. 105° C.
2-(Trifluoromethyl)-benzylidenemalononitrile, m.p. 46° C.
3-(Trifluoromethyl)-benzylidenemalononitrile, m.p. 81° C.
4-(Trifluoromethyl)-benzylidenemalononitrile, m.p. 109° C.
4-(2,2-Dimethylethyl)-benzylidenemalononitrile, m.p. 92° C.
3-Pyridinecarboxalidemalononitrile, m.p. 89° C.
2-Thiophenecarboxalidemalononitrile, m.p. 98° C.
3-Methoxybenzylidenemalononitrile, m.p. 102° C.
3-Trifluoromethoxybenzylidenemalononitrile, m.p. 73° C.
3-Chloro-4-fluorobenzylidenemalononitrile, m.p. 111° C.
3-Bromo-4-fluorobenzylidenemalononitrile, m.p. 122.5° C.
3-Carbomethoxybenzylidenemalononitrile, m.p. 125° C.
3-Hydroxybenzylidenemalononitrile, m.p. 152° C.
2-Cyano-(3-nitrophenyl)propenamide, m.p. 140° C.
3,4-Dichlorobenzylidenemalonitrile, m.p. 154° C.
3,4-Dimethoxybenzylidenemalonitrile, m.p. 137° C.
3,4-(Methylenedioxy)benzylidenemalonitrile, m.p. 201°–202° C.
4-Chloro-3-nitrobenzylidenemalonitrile, m.p. 142° C.
2-Nitro-4-thiophenecarboxalidemalonitrile, m.p. 103°–104° C.
α-Methanesulphonyl-3-nitrocinnamonitrile, m.p. 157° C.
4-Fluoro-3-nitrobenzylidenemalonitrile, m.p. 117° C.
4-(1-Piperidino)-3-nitrobenzylidenemalonitrile, m.p. 154° C.

EXAMPLE 2

1-Naphthol (1.44 g) was stirred in ethanol (20 ml) at ambient temperature. To this suspension was added 3-(trifluoromethyl)-benzylidenemalononitrile (2.23 g) and piperidine (1 ml). All solids dissolved and heat was evolved. Crystals of 2-amino-4-[3-(trifluoromethyl)-phenyl]-4H-naphtho[1,2-b]pyran-3-carbonitrile came out of solution after a few minutes and were collected by filtration after one hour's further stirring, were washed with ethanol and dried. Recrystallisation from ethanol gave white crystals, m.p. 215.5°–216.5° C.

The following compounds were prepared in a similar manner:

Ethyl 2-amino-4-[3-(trifluoromethyl)phenyl]-4H-naphtho[1,2-b]pyran-3-carboxylate, m.p. 156.5°–157° C.
Ethyl 2-amino-4-[4-(trifluoromethyl)phenyl]-4H-naphtho[1,2-b]pyran-3-carboxylate, m.p. 124°–126° C.
Ethyl 2-amino-4-[2-(trifluoromethyl)phenyl]-4H-naphtho[1,2-b]pyran-3-carboxylate, m.p. 144°–146° C.
2-Amino-4-(2-nitrophenyl)-4H-naphtho[1,2-b]pyran-3-carbonitrile, m.p. 142°–143.5° C.
2-Amino-4-(3-nitrophenyl)-4H-naphtho[1,2-b]pyran-3-carbonitrile, m.p. 214.5°–216° C.
2-Amino-4-(4-nitrophenyl)-4H-naphtho[1,2-b]pyran-3-carbonitrile, m.p. 229°–231° C.
2-Amino-4-[2-(trifluoromethyl)phenyl]-4H-naphtho[1,2-b]pyran-3-carbonitrile, m.p. 239°–240° C.
2-Amino-4-[3-(trifluoromethyl)phenyl]-4H-naphtho[1,2-b]pyran-3-carbonitrile, m.p. 215.5°–216.5° C.
2-Amino-4-[4-(trifluoromethyl)phenyl]-4H-naphtho[1,2-b]pyran-3-carbonitrile, m.p. 234°–239.5° C.
2-Amino-6-chloro-4-[3-(trifluoromethyl)phenyl]-4H-naphtho[1,2-b]pyran-3-carbonitrile, m.p. 179°–181° C.
2-Amino-6-methoxy-4-[3-(trifluoromethyl)phenyl]-4H-naphtho[1,2-b]pyran-3-carbonitrile, m.p. 216°–218° C.
2-Amino-4-(3-fluorophenyl)-4H-naphtho[1,2-b]pyran-3-carbonitrile, m.p. 240°–242° C.
2-Amino-4-(3-bromophenyl)-4H-naphtho[1,2-b]pyran-3-carbonitrile, m.p. 234°–235.5° C.
2-Amino-4-(3-chlorophenyl)-4H-naphtho[1,2-b]pyran-3-carbonitrile, m.p. 226°–228° C.
2-Amino-4-[4-(2,2-dimethylethyl)phenyl]-4H-naphtho[1,2-b]pyran-3-carbonitrile, m.p. 240°–243° C.
2-Amino-4-(3-pyridinyl)-4H-naphtho[1,2-b]pyran-3-carbonitrile, m.p. 205°–207° C.
Ethyl 2-amino-4-(3-nitrophenyl)-4H-naphtho[1,2-b]pyran-3-carboxylate, m.p. 152.5°–153.5° C.
2-Amino-4-(3-nitrophenyl)-4H-naphtho[1,2-b]pyran-3-carboxamide, m.p. 205°–206.5° C.
2-Amino-7-methoxy-4-(3-nitrophenyl)-4H-naphtho[1,2-b]pyran-3-carbonitrile, m.p. 242°–246° C.
2-Amino-8-methoxy-4-(3-nitrophenyl)-4H-naphtho[1,2-b]pyran-3-carbonitrile, m.p. 234°–236° C.
2-Amino-9-methoxy-4-(3-nitrophenyl)-4H-naphtho[1,2-b]pyran-3-carbonitrile, m.p. 244°–245° C.
2-Amino-3-cyano-4-(3-nitrophenyl)-4H-naphtho[1,2-b]pyran-6-carboxylic acid, m.p. 244°–248° C.
2-Amino-3-cyano-4-(3-methoxyphenyl)-4H-naphtho[1,2-b]pyran-6-carboxylic acid, m.p. 280° C. (decomposition).
2-Amino-3-cyano-4-(3-hydroxyphenyl)-4H-naphtho[1,2-b]pyran-6-carboxylic acid, m.p. 252°–256° C.
2-Amino-3-cyano-4-[3-(trifluoromethoxy)phenyl]-4H-naphtho[1,2-b]pyran-6-carboxylic acid, m.p. 253°–254.5° C.
2-Amino-3-cyano-4-(3-carboxyphenyl)-4H-naphtho[1,2-b]pyran-6-carboxylic acid, m.p. >300° C. (decomposition).
2-Amino-4-(3-methoxyphenyl)-4H-naphtho[1,2-b]pyran-3-carbonitrile, m.p. 139°–142.5° C.
2-Amino-4-(3-carbomethoxyphenyl)-4H-naphtho[1,2-b]pyran-3-carbonitrile, m.p. 235°–236° C.
2-Amino-4-[3-(trifluoromethoxy)phenyl]-4H-naphtho[1,2-b]pyran-3-carbonitrile, m.p. 194.5°–196.5° C.
2-Amino-4-(3-chloro-4-fluorophenyl)-4H-naphtho[1,2-b]pyran-3-carbonitrile, m.p. 211°–211.5° C.
2-Amino-4-(3-bromo-4-fluorophenyl)-4H-naphtho[1,2-b]pyran-3-carbonitrile, m.p. 209.5°–210.5° C.
2-Amino-7-hydroxy-4-(3-nitrophenyl)-4H-naphtho[1,2-b]pyran-3-carbonitrile, m.p. 237°–239° C.
2-Amino-4-(4-chloro-3-nitrophenyl)-4H-naphtho[1,2-b]-3-carbonitrile, m.p. 249°–251° C.
[2-Amino-4-(3-nitrophenyl)-4H-naphtho[1,2-b]pyran-3-yl]methyl sulphone, m.p. 173° C.
2-Amino-4-(2-nitro-4-thienyl)-4H-naphtho[1,2-b]pyran-3-carbonitrile, m.p. 187°–188° C.
2-Amino-4-(4-fluoro-3-nitrophenyl)-4H-naphtho[1,2-b]pyran-3-carbonitrile, m.p. 218°–220° C.
2-Amino-4-(3,4-methylenedioxyphenyl)-4H-naphtho[1,2-b]pyran-3-carbonitrile, m.p. 249°–252° C.
2-Amino-4-(3,4-dimethoxyphenyl)-4H-naphtho[1,2-b]pyran-3-carbonitrile, m.p. 207°–209.5° C.
2-Amino-4-(3,4-dichlorophenyl)-4H-naphtho[1,2-b]pyran-3-carbonitrile, m.p. 247°–249° C.

EXAMPLE 3

3-Nitrobenzaldehyde (84.5 g) and malononitrile (37 g) in ethanol (560 ml) were heated to reflux temperature, with stirring. The heating was halted, piperidine (10 drops) was added and the solution was further heated for 15 minutes. This solution was cooled to 5° C., using an ice-water bath, and to the resultant stirred suspension of intermediate 1-naphthol (80.7 g) was added, followed by piperidine (15 ml). This suspension was heated, under reflux, for 10 minutes and stirred to ambient temperature. The cream crystals of 2-amino-4-(3-nitrophenyl)-4H-naphtho[1,2-b]pyran-3-carbonitrile were filtered off, washed with ethanol until all colour had been removed, and dried, m.p. 214.5°–216° C.

EXAMPLE 4

2-Amino-4-(3-nitrophenyl)-4H-naphtho[1,2-b]pyran-3-carbonitrile (10.3 g) was dissolved in dry dimethylformamide (60 ml) and cooled with stirring, to 0° C. in an ice-water bath. Acetyl chloride (12.4 ml) was added, followed by pyridine (14.3 ml). After stirring for three days at ambient temperature the solids that initially had precipitated had redissolved to give a brown viscous solution. This solution was partitioned between brine and chloroform, the chloroform extract was washed with more brine, dried with magnesium sulphate, filtered and evaporated to dryness.

The residue was dissolved in a minimum of chloroform, passed through a 'flash' silica column and chloroform and the fractions containing product were bulked, evaporated and triturated with ether and a little methanol. The yellow 2-diacetylamino-4-(3-nitrophenyl)-4H-naphtho[1,2-b]pyran-3-carbonitrile was filtered off and washed with ether, m.p. 153°–154° C.

The following compound was prepared in a similar manner:

2-Diacetylamino-4-[3-(trifluoromethyl)phenyl]-4H-naphtho[1,2-b]pyran-3-carbonitrile, m.p. 138.5°–139° C.

EXAMPLE 5

2-Diacetylamino-4-(3-nitrophenyl)-4H-naphtho[1,2-b]pyran-3-carbonitrile (3.62 g) was dissolved in chloroform (200 ml) and mechanically stirred in the presence of Grade III alumina (36 g) for 24 hours at ambient temperature. The suspension was filtered, the alumina pad was washed through with 5% methanol in chloroform, the combined filtrates were evaporated and the residue was triturated with a little chloroform. The white solid was dissolved in dioxan (50 ml) and left to stand for 24 hours. An impurity precipitated out and this was filtered off. Water was added (200 ml) to the filtrate and the solid produced was filtered off, washed with water and dried. This solid was passed through a chloroform—'flash' silica column. The fractions containing product were bulked, evaporated to dryness and triturated with methanol to give yellow crystals of 2-acetamido-4-(3-nitrophenyl)-naphtho[1,2-b]pyran-3-carbonitrile, m.p. 234.5°–236° C.

EXAMPLE 6

2-Amino-4-(3-chloro-4-fluorophenyl)-4H-naphtho[1,2-b]pyran-3-carbonitrile (3.12 g) was heated, under reflux, in triethyl orthoformate (40 ml) for 24 hours. A fraction coming over at 80° to 140° C. was distilled off and more triethyl orthofomate (40 ml) was added, and the refluxing was continued for a further 24 hours. The solution was evaporated to dryness. The gummy residue was dissolved in chloroform and passed through a column of 'flash' silica using 30% hexane in chloroform as eluant. The fractions containing product were bulked, evaporated and triturated with ethyl acetate to give white crystals of 4-(3-chloro-4-fluorophenyl)-2-ethoxymethyleneamino-4H-naphtho[1,2-b]pyran-3-carbonitrile, m.p. 146°–148° C.

Similarly produced were:
2-Ethoxymethyleneamino-4-(3-nitrophenyl)-4H-naphtho[1,2-b]pyran-3-carbonitrile, m.p. 181.5°–183° C.
4-(4-Chloro-3-nitrophenyl)-2-ethoxymethyleneamino-4H-naphtho[1,2-b]pyran-3-carbonitrile, m.p. 184.5°–186° C.

EXAMPLE 7

2-Amino-4-(4-chloro-3-nitrophenyl)-4H-naphtho[1,2-b]pyran-3-carbonitrile (3.8 g) was dissolved in tetrahydrofuran (30 ml), at room temperature. To this was added pyridine (2.02 ml) followed by succinyl chloride (1.34 ml) and the solution was stirred for 24 hours. More pyridine (2.02 ml) and succinyl chloride (1.34 ml) was added. The solution was heated under reflux for 6 hours, cooled, poured into water and partitioned into chloroform. The chloroform extract was washed with brine, dried with magnesium sulphate, passed through a column of silica gel using 30% hexane in chloroform as eluant, evaporated to dryness and triturated with ethyl acetate to give 1.07 g of 4-(4-chloro-3-nitrophenyl)-2-(N-succinimido)-4H-naphtho[1,2-b]pyran-3-carbonitrile, m.p. 215.5°–217° C.

EXAMPLE 8

4-(4-Chloro-3-nitrophenyl)-2-ethoxymethyleneamino-4H-naphtho[1,2-b]pyran-3-carbonitrile (4.3 g) was dissolved in tetrahydrofuran (70 ml), and to this solution, with stirring, was added sodium borohydride (2.7 g), in portions. After one hour the suspension was cooled in ice-water and 1 molar hydrochloric acid (20 ml) was added dropwise, followed by water (200 ml). A yellow product was filtered off, washed with water and dried. This material was dissolved in hot chloroform and passed down a chloroform—'flash silica' column. Fractions containing product were bulked, evaporated to dryness, and triturated with ether to give 4-(4-chloro-3-nitrophenyl)-2-methylamino-4H-naphtho[1,2-b]pyran-3-carbonitrile, m.p. 278.5°–279° C.

EXAMPLE 9

2-Amino-4-(4-chloro-3-nitrophenyl)-4H-naphtho[1,2-b]pyran-3-carbonitrile (3.8 g) was dissolved in 2-butanone (100 ml). To this stirred solution was added dimethyl sulphate (2.4 ml) and potassium carbonate (3.5 g). This suspension was heated under reflux for two hours. More dimethyl sulphate (2.4 ml) and potassium carbonate (3.5 g) were added. The solution was heated for an additional 22 hours, cooled, filtered, evaporated to dryness, the residue was dissolved in warm chloroform and passed through a 'flash' chromatography column using 20% hexane-chloroform (1 liter) then further eluted with 10% hexane-chloroform (1 liter). The elution was then completed using chloroform. The fractions containing product were bulked, evaporated to dryness and the residue triturated with diethyl ether. Recrystallisation from toluene gave yellow crystals of 4-(4-chloro-3-nitrophenyl)-2-dimethylamino-4H-naphtho[1,2-b]pyran-3-carbonitrile, m.p. 217.5°–218.5° C.

EXAMPLE 10

4-(4-Chloro-3-nitrophenyl)-2-(N-succinimido)-4H-naphtho[1,2-b]pyran-3-carbonitrile (0.41 g) was dissolved in tetrahydrofuran (20 ml). To this solution 2M sodium hydroxide was added (0.94 ml) and the solution was stirred for two days, at ambient temperature. The solution was evaporated to dryness and the residue was dissolved in water (50 ml) and filtered. To the filtrate acetic acid (1.14 ml) was added and the precipitated buff N-[4-(4-chloro-3-nitrophenyl)-3-cyano-4H-naphtho[1,2-b]pyran-2-yl]-succinamic acid was filtered off, washed with water and dried, m.p.>300° C.

EXAMPLE 11

Soft gelatin capsule

Each soft gelatin capsule contains:

| Active ingredient | 150 mg |
|---|---|
| Arachis oil | 150 mg |

After mixing together, the blend is filled into soft gelatine capsules using the appropriate equipment.

EXAMPLE 12

Hard gelatin capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 13

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 14

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 15

The concanavalin A response of rat spleen cells was used as a primary in vitro assay to determine the activity of the compounds of the invention. Many methods for the determination of concavalin A response are described in the literature. The method employed was similar to that described by Lacombe P. et al, FEBS 3048 191, 227-230. We used $2 \times 10^5$ cells per culture well, and concanavalin A was employed at 1 μg/ml. 2-Mercaptoethanol was a requirement ($2 \times 10M^{-5}$) and 0.25 μCi of tritiated thymidine was added 6 hours before cell harvesting.

The following compounds have an IC$_{50}$ in the range of from 0.006 to 2.0 μM

Ethyl 2-amino-4-(3-nitrophenyl)-4H-naphtho[1,2-b]pyran-3-carboxylate.
2-Amino-4-(3-nitrophenyl)-4H-naphtho[1,2-b]pyran-3-carbonitrile.
2-Amino-9-methoxy-4-(3-nitrophenyl)-4H-naphtho[1,2-b]pyran-3-carbonitrile.
2-Amino-4-[3-(trifluoromethyl)phenyl]-4H-naphtho[1,2-b]pyran-3-carbonitrile.
2-Diacetylamino-4-[3-(trifluoromethyl)phenyl]-4H-naphtho[1,2-b]pyran-3-carbonitrile.
2-Amino-4-(3-chlorophenyl)-4H-naphtho[1,2-b]pyran-3-carbonitrile.
2-Amino-4-(3-fluorophenyl)-4H-naphtho[1,2-b]pyran-3-carbonitrile.
2-Amino-4-(3-pyridinyl)-4H-naphtho[1,2-b]pyran-3-carbonitrile.
2-Amino-4-(3-carbomethoxyphenyl)-4H-naphtho[1,2-b]pyran-3-carbonitrile.
2-Amino-4-(3-chloro-4-fluorophenyl)-4H-naphtho[1,2-b]pyran-3-carbonitrile.
2-Amino-4-(4-chloro-3-nitrophenyl)-4H-naphtho[1,2-b]pyran-3-carbonitrile.
2-Amino-4-(3-trifluoromethoxyphenyl)-4H-naphtho[1,2-b]pyran-3-carbonitrile.

We claim:

1. A compound of the formula

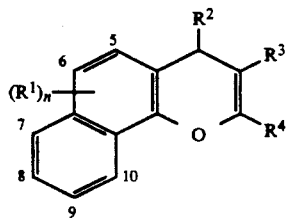

in which
n is 0, 1 or 2 and $R^1$ is attached at any of the positions 5, 6, 7, 8, 9 or 10, and each $R^1$ is halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —COOR$^5$ where R$^5$ is an ester group, —CONR$^6$R$^7$ or —NR$^6$R$^7$ where R$^6$ and R$^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —COOR$^8$ where R$^8$ is an ester group, —CONR$^9$R$^{10}$ where R$^9$ and R$^{10}$ are each hydrogen or $C_{1-4}$ alkyl, or R$^{11}$SO$_2$— where R$^{11}$ is $C_{1-4}$ alkyl or optionally substituted phenyl; and $R^4$ is —NR$^{12}$R$^{13}$, —NHCOR$^{12}$, —N(COR$^{12}$)$_2$ or —N=CHOR$^{12}$ where R$^{12}$ and R$^{13}$ are each hydrogen or $C_{1-4}$ alkyl optionally substituted with carboxy,

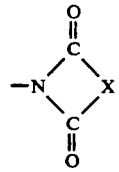

where X is $C_{2-4}$ alkylene, or —NHSO$_2$R$^{14}$ where R$^{14}$ is $C_{1-4}$ alkyl or optionally substituted phenyl;

provided that when n is 0, R$^3$ is nitrile and R$^4$ is —NH$_2$, R$^2$ is not phenyl or phenyl substituted in the para-position with a single chloro, hydroxy or methoxy substituent;

or a salt thereof.

2. A compound according to claim 1 in which n is 0, 1 or 2 and R$^1$ is attached at any of the positions 5, 6, 7, 8, 9 or 10, and each R$^1$ is halo, trifluoromethyl or $C_{1-4}$ alkoxy, R$^2$ is phenyl, naphthyl or heteroaryl optionally substituted with one or two substituents each selected from nitro, trifluoromethyl, halo, $C_{1-4}$ alkyl and $C_{1-4}$ alkoxy or R$^2$ is furanyl optionally substituted with $C_{1-4}$ alkyl, R$^3$ is nitrile, carboxy, —COOR$^8$ where R$^8$ is an ester group, or —CONR$^9$R$^{10}$ where R$^9$ and R$^{10}$ are each hydrogen or $C_{1-4}$ alkyl, and R$^4$ is —NR$^{12}$R$^{13}$, —NHCOR$^{12}$ or —N(COR$^{12}$)$_2$ where R$^{12}$ and R$^{13}$ are each hydrogen or $C_{1-4}$ alkyl, or $-NHSO_2R^{14}$ where $R^{14}$ is $C_{1-4}$ alkyl or phenyl optionally substituted with one to three substituents each selected from $C_{1-4}$ alkyl, $C_{1-4}$ alkoxy, nitro and halo; provided that when n is 0, $R^3$ is nitrile and $R^4$ is $-NH_2$, $R^2$ is not phenyl or phenyl substituted in the para-position with a single chloro, hydroxy or methoxy substituent.

3. A compound according to claim 1 in which n is 0 or 1 and $R^1$ is $C_{1-4}$ alkoxy or halo.

4. A compound according to claim 3 in which $R^2$ is phenyl optionally substituted with one or two substituents selected from halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, $-COOR^{15}$ where $R^{15}$ is an ester group, $-CONR^{16}R^{17}$ or $-NR^{16}R^{17}$ where $R^{16}$ and $R^{17}$ are each hydrogen or $C_{1-4}$ alkyl.

5. A compound according to claim 4 in which $R^3$ is nitrile.

6. A compound according to claim 5 in which $R^4$ is $-NH_2$.

7. A pharmaceutical formulation comprising a compound according to claim 1, or a pharmaceutically-acceptable salt thereof, together with a pharmaceutically-acceptable diluent or carrier therefor.

8. A method of treating an immune disease or a disease in which excess cell proliferation or enzyme release occur, which comprises administering to a patient in need of treatment a therapeutic dosage of a compound according to claim 1.

9. A method of treating restenosis, which comprises administering to a patient in need of treatment a therapeutic dosage of a compound of claim 1.

10. The method of claim 9 wherein said administration is by local delivery.

11. The method of claim 10 where the local delivery is by means of a local delivery catheter.

12. The method of claim 10 where the local delivery is by means of a site specific carrier.

13. The method of claim 10 wherein said administration is by a membrane anchored linker.

14. The method of use of claim 10 where the local delivery is by means of an implant.

15. A method of inhibiting vascular smooth muscle cell proliferation, which comprises administering to a patient in need of treatment a therapeutic dosage of a compound of claim 1.

* * * * *